US007947081B2

(12) United States Patent
Linares

(10) Patent No.: US 7,947,081 B2
(45) Date of Patent: May 24, 2011

(54) SKELETAL IMPLANT FOR REPLACING A HUMAN BONE

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 325 days.

(21) Appl. No.: 12/171,465

(22) Filed: Jul. 11, 2008

(65) Prior Publication Data

US 2009/0018657 A1   Jan. 15, 2009

Related U.S. Application Data

(60) Provisional application No. 60/949,051, filed on Jul. 11, 2007.

(51) Int. Cl.
*A61F 2/30* (2006.01)
*A61F 2/38* (2006.01)
*A61F 2/32* (2006.01)
*A61F 2/28* (2006.01)

(52) U.S. Cl. .............. 623/18.11; 623/20.14; 623/22.11; 623/23.39; 623/23.44; 623/23.51

(58) Field of Classification Search .............. 623/18.11, 623/19.11–19.14, 20.11–20.17, 20.21–20.22, 623/20.24, 20.3–20.36, 22.11, 22.13–22.15, 623/22.4–22.46, 23.15–23.44, 23.51
See application file for complete search history.

(56) References Cited

U.S. PATENT DOCUMENTS

| 3,683,424 | A | * | 8/1972 | Pangman | 623/8 |
| 4,280,233 | A | * | 7/1981 | Raab | 623/23.59 |
| 4,714,477 | A | | 12/1987 | Fichera et al. | |
| 5,007,934 | A | | 4/1991 | Stone | |
| 5,092,898 | A | | 3/1992 | Bekki et al. | |
| 5,607,311 | A | * | 3/1997 | Browne-Wilkinson | 434/274 |
| 5,964,783 | A | * | 10/1999 | Grafton et al. | 606/232 |
| 6,471,519 | B1 | * | 10/2002 | Biermann et al. | 434/274 |
| 6,627,141 | B2 | | 9/2003 | McNulty et al. | |
| 6,692,679 | B1 | | 2/2004 | McNulty et al. | |
| 6,800,298 | B1 | | 10/2004 | Burdick et al. | |
| 6,800,670 | B2 | | 10/2004 | Shen et al. | |
| 6,818,172 | B2 | | 11/2004 | King et al. | |
| 7,109,181 | B2 | | 9/2006 | Cowlen et al. | |
| 7,148,209 | B2 | | 12/2006 | Hoemann et al. | |
| 7,179,298 | B2 | | 2/2007 | Greenlee | |

(Continued)

OTHER PUBLICATIONS

Bone & Joint Clinic of Houston. "Hip and Knee Joint Replacement". Hip and Knee Joint Replacement—Bone and Joint Clinic of Houston, Service, hip. Downloaded from <http://www.bjc-houston.com/hip/> on Sep. 2, 2010.*

*Primary Examiner* — David Isabella
*Assistant Examiner* — Andrew Iwamaye
(74) *Attorney, Agent, or Firm* — Gifford, Krass, Sprinkle, Anderson & Citkowski, P.C.

(57) ABSTRACT

A skeletal implant for replacing a human bone includes an inner reinforcing member and an outer plasticized and fluid resistant layer encasing the inner reinforcing member. A structurally rigid and foamable layer is disposed between the inner reinforcing member and the outer plasticized layer. An end of the outer layer is configured for receiving, in articulated engagement, an end of an adjoining bone. A plurality of ligaments are grafted between the implant and the adjoining bone and proximate the articulated engagement. Conduit passageways are also established between the inner reinforcing member and the end of the outer layer in order to communicate a fluid to an articulating engagement and ligament supporting location with an adjoining bone.

6 Claims, 2 Drawing Sheets

U.S. PATENT DOCUMENTS

| | | |
|---|---|---|
| 7,186,364 B2 | 3/2007 | King et al. |
| 7,384,430 B2 | 6/2008 | Greer et al. |
| 2003/0060890 A1* | 3/2003 | Tarabishy .................. 623/22.12 |
| 2003/0060891 A1* | 3/2003 | Shah ........................... 623/22.13 |
| 2004/0068322 A1 | 4/2004 | Ferree |
| 2005/0055101 A1* | 3/2005 | Sifneos ...................... 623/20.32 |
| 2005/0131546 A1* | 6/2005 | Mor ........................... 623/22.11 |
| 2007/0088442 A1* | 4/2007 | Cima et al. ................. 623/18.11 |
| 2007/0166670 A1* | 7/2007 | Sakezles ......................... 434/86 |
| 2008/0114096 A1* | 5/2008 | Qu et al. ......................... 524/18 |
| 2009/0216327 A1* | 8/2009 | Miller et al. ............... 623/16.11 |

* cited by examiner

US 7,947,081 B2

SKELETAL IMPLANT FOR REPLACING A HUMAN BONE

CROSS-REFERENCE TO RELATED APPLICATIONS

This Application is a Non-Provisional of Provisional (35 USC 119(e)) and claims the priority of U.S. Provisional Patent Application Ser. No. 60/949,051 filed on Jul. 11, 2007, entitled Skeletal Implant for Replacing a Human Bone.

FIELD OF THE INVENTION

The present invention is a skeletal implant for use in replacing a human bone. In particular, the implant of the present invention is an improvement over prior art implants, typically those constructed of a metallic or other synthetic material, in that it provides for improved in-molding of ligaments (such as for attaching to existing bones) as well as over-molding at selected ends to provide additional support for such attachment, in addition to permitting the introduction of human-replicated fluids into the implant structure and to better assist in replicating the features of a human bone.

BACKGROUND OF THE INVENTION

Prosthetic implants are well known in the art. Such include artificially installed hip joints and the like.

A disadvantage of known implants includes the inadequate (or non-existent) use of ligaments to assist in incorporating the artificial bone implant into an effectively working component of a skeletal structure. In particular, existing prior art implants do not effectively address the need to incorporate an artificial implant (this replacing an existing/damaged natural bone or prior synthetic implant) in cooperating use with an existing bone, and such as by employing improved ligament connecting and/or lubricating structure in order to achieve a more effective and functional device.

SUMMARY OF THE INVENTION

The present invention discloses a skeletal implant for replacing a human bone, and which is an improvement over prior art implants in that it provides for a more effective and dynamically interactive implant, such as when incorporated for use with existing/remaining bone structure. The implant includes an inner reinforcing member and an outer plasticized and fluid resistant layer encasing the inner reinforcing member.

A structurally rigid and foamable layer is disposed between the inner reinforcing member and the outer plasticized layer. An end of the outer layer is configured for receiving, in articulated engagement, an end of an adjoining bone.

A plurality of ligaments are grafted between the implant and the adjoining bone and proximate the articulated engagement. Conduit passageways are also established between the inner reinforcing member and the end of the outer layer in order to communicate a fluid to an articulating engagement and ligament supporting location with an adjoining bone.

Additional features include the inner reinforcing member incorporating a metal insert. An inlet valve is further disposed upon the outer layer and communicates the fluid to at least the inner reinforcing member. The implant end also exhibits a three-dimensional and over-molded configuration, such as which may further include a plurality of alternating peaks and valleys and which, in cooperation with the ligament structure and fluid lubricant supply, ergonomically interact the implant with an existing bone.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 1:
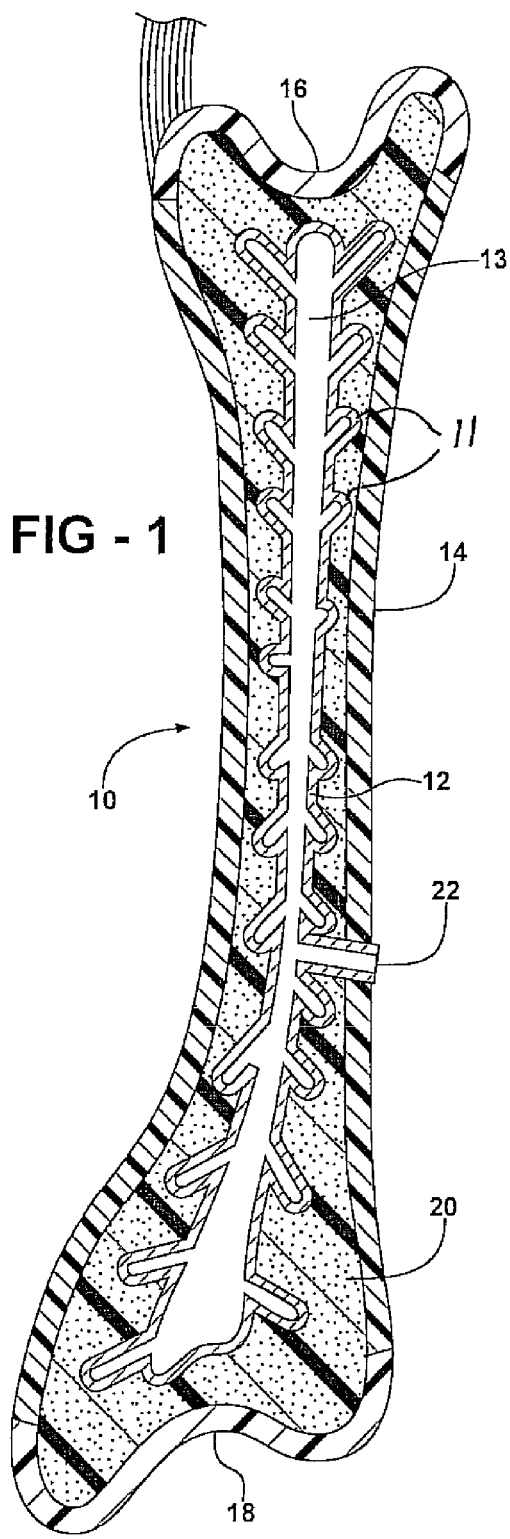
FIG. 1 is a cutaway illustration of a skeletal implant according to a preferred embodiment of the present invention.

Referring now to FIG. 1, a skeletal implant is generally illustrated in cutaway at 10 according to a first preferred embodiment of the present invention. As previously described, the skeletal implant is intended to operate as a replacement for human bone structure (such as resulting from disease, accidents, etc.) and which is further an improvement over existing prosthetic metal implants and the like in that it provides a more effective implant, in particular when incorporated into a joint and ligament supported engagement with existing bone structure.

The implant 10 includes the features of an internally positioned and reinforcing member 12, the general configuration of which typically corresponds to that of the overall implant 10. As shown in FIG. 1, the inner reinforcing member 12 is typically slightly less in overall dimension (accounting for the ergonomically configuring and ligament defining ends associated with the implant) and is also likely angled/contoured to match the desired overall configuration of the implant.

In a preferred embodiment, the reinforcing member 12 is a metal reinforcing structure exhibiting a central elongated (and as described above typically a somewhat arcuate shaped) body. In the example illustrated, a plurality of scales 11 or other suitable shaped protuberances are defined along part (or all) of the overall length of the reinforcing member 12, scales providing both reinforcing and positional stabilizing features to the inner reinforcing member 12. It is also envisioned that a fluid 13 (such as which is consistent with that associated with normal human bones) can be encapsulated within the reinforced member and/or, as further discussed, also be supplied through a conduit passageway established with an open interior of the reinforcing member 12.

It is also envisioned that the reinforcing member 12, in addition to being a metal such as an aluminum, can be constructed of other materials exhibiting the necessary properties of strength, weight, resiliency, fluid retention/sealing and durability, such as including certain types of plastics or polymers. In one instance, a molding process can be employed by which a powdered thermoplastic resin is formed into a defined shape. Such molding processes can include injection molding, compression molding, reaction injection molding (RIM), as well as other manual/cold molding/pouring processes. The result is a strengthened plastic composite which exhibits properties comparable to those of steel.

Surrounding and encasing the reinforcing member 12 is an outer layer 14, this including in one non-limited application such as an antimicrobial plastic material, the purpose of which is to assist in preventing the incidence of bacteria creation and/or infection, such as upon the implant 10 being inserted into the patient's body. Opposite end sections 16 and 18 of the outer layer 14 can further be constructed of a lubricated plastic composition, the purpose for which (as will be described in reference to succeeding figures) is to facilitate the ability of the ends of the implant 10 to smoothly and durably articulate in cooperation with end-engaging bones (either natural or implanted) in order to provide a maximum degree of comfort and motion.

Encircling the three-dimensional space between the metal reinforcing member 12 and the outer plastic layer 14 is a plasticized foam 20 which operates to positionally secure and strengthen the construction of the implant, as well as the positional arrangement and retention of the inner reinforcing member 14 in a spatially supported fashion relative to the outer layer 14. A number of materials are capable of being employed within the foam 20, these again including any of the molding constructions previously described, and in addition to numerous other potential materials which can be used separately or in combination with a number of foamable plastic compositions. Along these lines, it is also envisioned that an aggregate composition can be incorporated into the foam 20, such providing varying degrees of durability depending upon the desired implant performance parameters and/or desired application.

Also illustrated at 22 is the provision of a valve, accessible to the open interior of the reinforcing member 12, from the surface of the outer layer 14, and which provides a fluid injection port (location) associated with the inner reinforcing member 12 and/or the encircling foam 20. In this fashion, a fluid medium (not shown and which can include such as including a naturally reproduced bone fluid generated with natural bone structure) can be recycled for reuse. Other artificial fluids can also be substituted (or intermixed with a natural fluid) in order to provide varying performance characteristics to the implant and as will be subsequently described.

Figure 2:
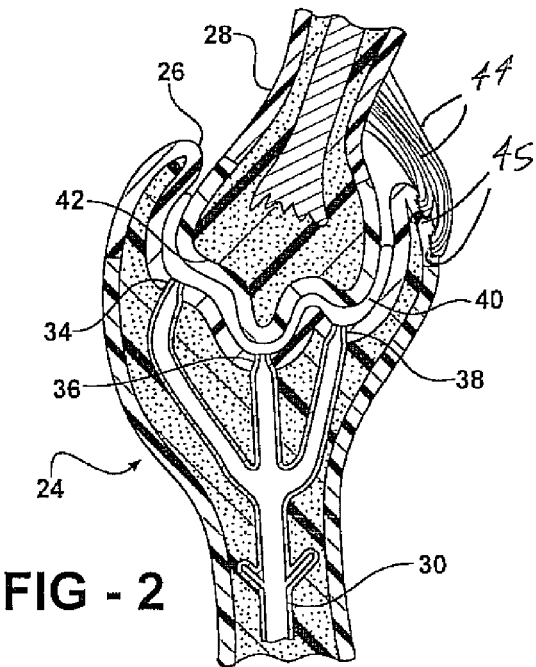
FIG. 2 is an enlarged end view illustration of the implant illustrated in FIG. 1 and further showing the features of the over-molded end for attaching to an existing bone, fluid-holding reinforcement insert and externally attached ligaments.

Referring now to FIG. 2, a sectional cutaway end view illustration is shown of an implant 24, similar to that illustrated in FIG. 1, and further showing the features of a composite plastic over-molded end 26 for encircling and receiving an opposing end of an existing bone 28. In particular, the implant 24 includes a suitable central reinforcing member (or spline) 30 similar to that described in FIG. 1, and again within which is contained a volume of a suitable (nourishing and/or lubricating) fluid medium 32.

An end of the implanted reinforcing member 30 communicates with the over-molded/socket end 26 of the implant 24, such as through communicating passages shown at 34, 36, and 38 (see also enlarged view FIG. 2B) and, in this fashion, communicates the fluid medium 32 with a spacing 40 established between the socket end 26 and an opposing surface 42, such as of the existing bone 28. As previously stated, it is also envisioned that the implant construction of the present invention can be utilized singularly (such as in cooperation with existing human bone). Alternatively, the implant structure of the present invention is also envisioned to be capable of being provided in articulated pairs (such as upper arm/forearm or femur/lower leg arrangements).

Figure 2A:
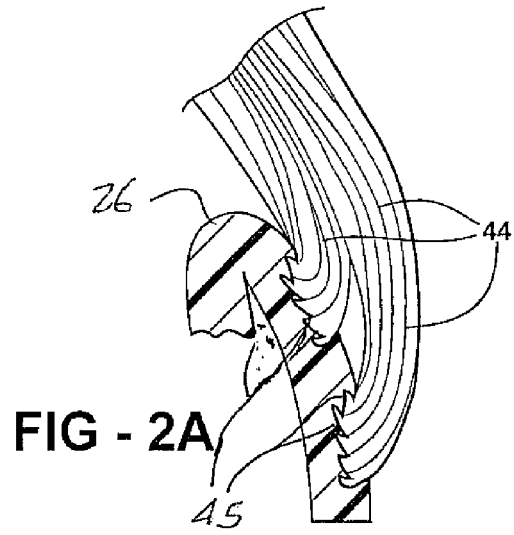
FIG. 2A is an enlarged sectional illustration of the ligament structure of FIG. 2 established between the skeletal implant and a connecting bone.
Figure 2B:
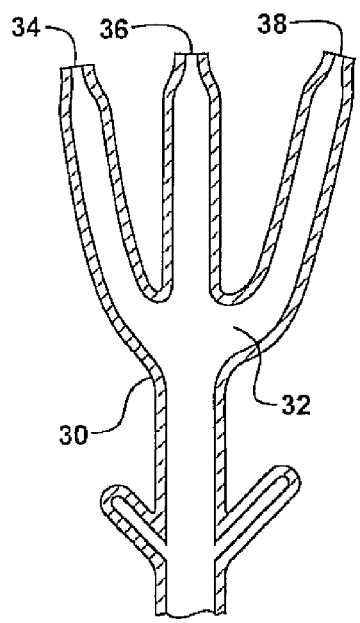
FIG. 2B is another enlarged sectional illustration of the reinforcing insert of FIG. 2 which is capable of holding a volume of injected fluid.

As again illustrated in FIGS. 2 and 2A, a series of ligaments 44 extend between (such as outer edge) locations associated with each of the over-molded implant end 26 and the existing bone end 42. The ligaments 44 can include both the natural variety of material (i.e., that harvested from actual bone and cartilage structure) as well as synthetically produced ligaments which can be implanted along with the skeletal implant structure.

As further shown in FIG. 2A, connecting end locations of the ligaments, see as shown at 45, can be in-molded (or otherwise resistively inter-fitted or engaged) with end locations associated with the over-molded end 26 of the implant 24. The ligaments 45 in this instance can potentially include natural ligaments associated with an existing bone for which it is desired to establish a substitute joint/socket arrangement with the newly substituted implant 24.

As is further known, ligaments are necessary for providing the necessary support and connection between adjoining bones, such as during the range of motion or pivoting of the bones within their socket connection. The ability to over-mold the socket end 26 of the implant 24, such as which establishes multiple (individual) areas of contact, further provides additional support when engaged with the succeeding bone 28 (either natural or implanted). It is further understood that the over-molded end adopts a three-dimensional configuration which further includes a plurality of alternating peaks and valleys formed along said implant end.

Figure 3:
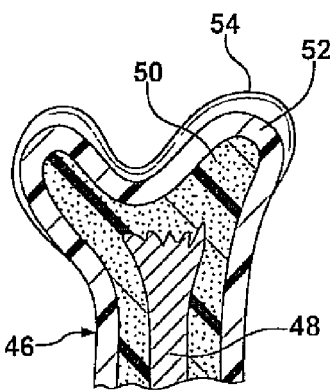
FIG. 3 is an enlarged end view illustration of a skeletal implant according to a further preferred embodiment of the present invention.

Referring now to FIG. 3, an enlarged end view illustration is shown of a skeletal implant 46 according to a further preferred embodiment of the present invention which includes an alternate variation of inner reinforcing member 48, encircling foamed plastic layer 50, and outer (fluid impervious and typically lubricous) composite plastic layer 52. An additional fluid residing/impregnated layer is again shown at 54 and which, as previously described, can be constructed of a polymer or other composite plastic and which facilitates a range of motion when established in a joint defining relationship with a succeeding and articulating bone.

Figure 3A:
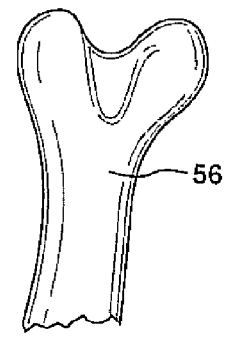
FIG. 3A is an illustration according to the prior art and which illustrates, in comparison to FIG. 3, an existing metal bone.

FIG. 3A is an illustration according to the prior art which illustrates, in comparison to FIG. 3, an existing metal bone 56. The purpose of this illustration is to highlight the compositional differences of the implants, such as shown at 10, 24 and 46 of the present inventions, in comparison to an existing bone implant according to the prior art.

Figure 4:
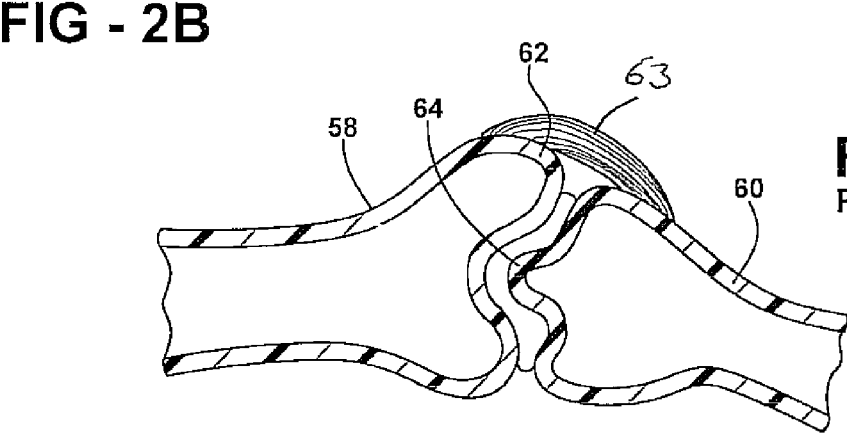
FIG. 4 is a further illustration according to the prior art and which illustrates an existing bone-to-bone connection.

FIG. 4 is a further illustration according to the prior art which illustrates an existing bone-to-bone connection as referenced by bones 58 and 60 with connecting ends 62 and 64 and associated ligaments 63. The bone structure referenced in FIG. 4, is estimated as only capable of safely absorbing a minimal (e.g. no more than 50 lb) crosswise directed impact force, at which point the surface attached (non in-molded) ligaments are likely to pull away (disengage from) the attachment locations with each bone 58 and 60.

Figure 5:
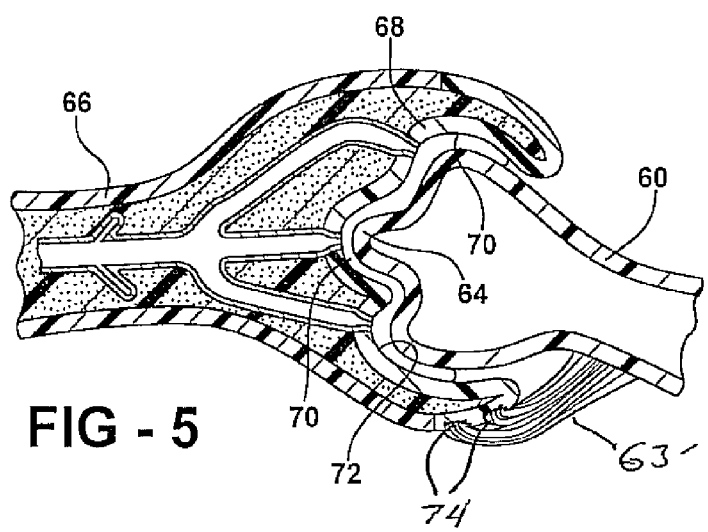
FIG. 5 is an illustration, similar in presentation to that shown in the prior art illustration of FIG. 4, and showing the over-molding of the skeletal implant end in order to provide additional support to the connection to such as an existing bone and according to the present invention.

Referring finally to FIG. 5, an illustration, similar in presentation to the prior art view shown in FIG. 4, and which illustrates an implant 66 with an over-molded and interiorly configured 68 end, this in comparison to the bone 58 shown in the previous prior art illustration, the implant 66 establishing an articulating contact with the end 64 associated with existing bone 60 also referenced in FIG. 4. As previously described, the over-molding of the skeletal implant end, such as by the creation of individual and interconnected arcuate configurations 68, 70 and 72, collectively define a recessed interior which interacts with the opposing end configuration 64 of the existing bone 60 to provide additional support to the sockete connection.

Ligaments are again employed, and which are illustrated at 63', these being similar to those shown at 63 in FIG. 4, with the exception that in-molding techniques can be employed (see further at 74) for more securely attaching ends of the ligaments to the implant 66, such as which can extend naturally from the bone 60. The implant 66 is otherwise constructed in a fashion similar to that described in reference to implants 10, 24 and 46, such that a repetitive description is unnecessary.

Having described my invention, other and additional preferred embodiments will become apparent to those skilled in the art to which it pertains, without deviating from the scope of the appended claims.

I claim:

1. A skeletal implant for replacing a human bone, said implant comprising:
   a continuous, three dimensional, and elongated extending member having a longitudinal axis extending from a proximal end to a distal end, wherein the proximal and distal ends are configured for articulating with a respective additional bone, at least one of the proximal end and distal end including an over-molded end defining a recessed interior adapted to support an end of the respective additional bone in a joint defining relationship;
   an inner reinforcing member and an outer plasticized and fluid resistant layer encasing said inner reinforcing member;
   an interior passageway defined within said inner reinforcing member and which supports a volume of an inserted lubricant;
   a fluid injection port and associated valve accessible to said interior passageway defined in said inner reinforcing member, from a surface of a surrounding outer layer, said valve configured to communicate said lubricant to said inner reinforcing member;
   a structurally rigid foam disposed between said inner reinforcing member and said outer plasticized layer; and
   a plurality of synthetic ligaments in-molded at outer edge locations as said over-molded end.

2. The implant as described in claim 1, said inner reinforcing member further comprising a metal insert.

3. The implant as described in claim 1, further comprising a plurality of conduit passageways established between said inner reinforcing member and said over-molded end in order to communicate said lubricant to an articulating engagement region established with the end of the respective additional bone.

4. The implant as described in claim 1, said over-molded end further comprising a plurality of alternating peaks and valleys.

5. The implant as described in claim 1, at least said structurally rigid foam further comprising at least one of an injection molded plastic, a compression molded plastic, a reacting injection molded plastic, and a manual/cold poured plastic.

6. The implant as described in claim 1, said outer plasticized layer further comprising at least one of an antimicrobial plastic and a lubricious plasticized end.

* * * * *